United States Patent
Ye et al.

(10) Patent No.: US 7,277,169 B2
(45) Date of Patent: Oct. 2, 2007

(54) WHOLE SPECTRUM FLUORESCENCE DETECTION WITH ULTRAFAST WHITE LIGHT EXCITATION

(75) Inventors: Jing Yong Ye, Ann Arbor, MI (US); Theodore B. Norris, Dexter, MI (US); James R. Baker, Jr., Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 11/355,387

(22) Filed: Feb. 16, 2006

(65) Prior Publication Data

US 2006/0187448 A1 Aug. 24, 2006

Related U.S. Application Data

(60) Provisional application No. 60/654,853, filed on Feb. 18, 2005.

(51) Int. Cl.
*G01N 21/64* (2006.01)
(52) U.S. Cl. .................... 356/317; 250/458.1
(58) Field of Classification Search ............. 356/317, 356/300, 311, 318, 417; 250/458.1, 459, 250/461.1, 461.2
See application file for complete search history.

(56) References Cited

U.S. PATENT DOCUMENTS 4,923,819 A * 5/1990 Fernandez et al. .......... 436/518

| | | | |
|---|---|---|---|
| 2003/0058440 A1* | 3/2003 | Scott et al. | 356/318 |
| 2003/0117618 A1* | 6/2003 | Itoh et al. | 356/317 |
| 2004/0150818 A1* | 8/2004 | Armstrong et al. | 356/301 |
| 2004/0190134 A1* | 9/2004 | Tahara et al. | 359/386 |

OTHER PUBLICATIONS

M. K. Reed, M. K. Steiner-Shepard, and D. Negus,Widely tunable femtosecond optical parametric amplifier at 250 kHz with a Ti:sapphire regenerative amplifier, Opt. Lett. 19, 1855 (1994); M. K. Reed, M. K. Steiner-Shepard, M. S. Armas, and D. Negus, J. Opt. Soc. Am. B 12, 2229 (1995).*

Bîhler, C. A., Graf, U., Hochstrasser, R. A. & Anliker, M. 1998□□Multidimensional Fluorescence spectroscopy using a streak□□camera based pulse fluorometer. Rev. Sci. Instr. 69, 1512-1518.*

(Continued)

*Primary Examiner*—Gregory J. Toatley, Jr.
*Assistant Examiner*—Rebecca C. Slomski
(74) *Attorney, Agent, or Firm*—Harness, Dickey & Pierce, P.L.C.

(57) ABSTRACT

A fluorescence detection system for testing a sample having at least one fluorophore. The fluorescence detection system comprises a white light generation system outputting a white light pulse. The white light pulse has a first frequency range and a first time duration. The white light pulse excites the at least one fluorophore of the sample to emit a fluorescence. The fluorescence has a second frequency range and a second time duration, wherein the first time duration is less than the second time duration. A time-resolving detector receives the fluorescence and at least a portion of the white light pulse and separates the fluorescence from the portion of the white light pulse.

26 Claims, 4 Drawing Sheets

OTHER PUBLICATIONS

J. Hermann, U. Griebner, N. Zhavoronkov, A. Husakou, D. Nickel, J.C. Knight, W.J. Wadsworth, P.St.J. Russel, G. Korn, Experimental Evidence for Supercontinuum Generation by Fission of Higher ORder Solitons in Photonic Fibers, Phys. Rev. Lett. 88, 173901 (2002).*

Weigand, R, H. Crespo, A. Dos Santos, P. Balcou "Time resolved study of the spectral characteristics of supercontinuum pulses propagating in scattering medium," Applied Physics B 77, 253-257 (2003).*

* cited by examiner

WHOLE SPECTRUM FLUORESCENCE DETECTION WITH ULTRAFAST WHITE LIGHT EXCITATION

CROSS-REFERENCE TO RELATED APPLICATIONS

This application claims the benefit of U.S. Provisional Application No. 60/654,853, filed on Feb. 18, 2005. The disclosure of the above application is incorporated herein by reference.

GOVERNMENT RIGHTS

This invention was made with government support under Contract No. NAS2-02069 awarded by the National Aeronautics and Space Administration. The Government has certain rights in the invention.

FIELD

The present disclosure relates to fluorescence measurements and, more particularly, relates to a method and apparatus for detecting multiple fluorophores using an ultrafast super continuum light source for excitation.

BACKGROUND AND SUMMARY

The statements in this section merely provide background information related to the present disclosure and may not constitute prior art.

Fluorescence measurements are an invaluable tool for a wide variety of applications in various fields, including analytical chemistry, biochemistry, cell biology, physiology, cardiology, photochemistry, environmental science, and other basic science and clinical research. A primary advantage of fluorescence measurement over absorption measurement is its high selectivity and sensitivity. For example, the dynamics of protein folding and unfolding can be studied using single-molecule fluorescence detection. High throughput fluorescence screening can be performed to find potential drug leads from an extensive library of compounds. Fluorescence emission from ions can be used to quantify their local concentrations in living cells. Membrane structure and function can be studied with fluorescence probes. Drug delivery and its treatment effects can be monitored in living biological systems. Minute traces of fluorescent materials can be detected and identified for forensic science and homeland security. Binding properties of biochemical species can be monitored in real time and in situ by fluorescence measurements.

In an attempt to address the variety of fluorescence-based measurements, some detection instruments have been used in both research institutions and industry. One such instrument employs fluorescence microscopy, which has become one of the most rapidly expanding microscopy techniques employed today, both in medical and biological sciences. In fluorescence microscopy, fluorescent dyes are used to label specific subcellular components, which can then be optically imaged. Similarly, a number of microscopes and fluorescence accessories have been developed, such as laser scanning confocal microscopes and multiphoton fluorescence microscopes, to aid in such imaging. Different from fluorescence imaging, flow cytometers have been used to measure the total fluorescence from each cell to enable large populations of cells to be studied, thereby providing quantitative information on many important biological processes (e.g. receptor expression, analysis of intracellular proteins, targeted drug uptake, etc.). Despite the broad applications of fluorescence measurements and a long history of the development of various kinds of fluorescence detection systems, the basic detection mechanism remains unchanged until now.

One of the most important considerations for a fluorescence detection system is to separate fluorescence signals from excitation light. As a basic fluorescence nature, fluorescence emission occurs at a longer wavelength due to the Stokes shift when certain molecules have absorbed excitation photons of shorter wavelengths. Emission filters are often used to screen out the stray light such as Rayleigh and Raman scatter from the sample under excitation and from other components in the optical path, allowing primarily the wavelength of fluorescence light specific to the sample to pass through. Often limited by the small Stokes shift, some fluorescence signal has to be sacrificed in order to completely block the stray light, thus preventing a whole fluorescence spectrum from being observed. In addition, both absorption and emission are unique characteristics of a particular molecule. Thus, with a single excitation wavelength, such as a laser source, only a limited number of fluorophores that have absorption matched with the excitation wavelength can be excited and thus detected. Even if some broadband light sources, such as xenon lamps, are sometimes used for excitation, excitation filters are often used, which allows a selected band of light energy to pass through and excite the sample while blocking other wavelengths, especially those in the emission spectrum. Therefore, the types of fluorophores that can be simultaneously excited are limited in this case. These drawbacks in conventional fluorescence measurements have not only reduced the detection speed and sensitivity, but have also limited the selection of detectable fluorescent markers.

According to the principles of the present teachings, a fluorescence detection system for testing a sample having at least one fluorophore is provided having advantageous construction. The fluorescence detection system comprises a white light generation system outputting a white light pulse. The white light pulse has a first frequency range and a first time duration. The white light pulse excites the at least one fluorophore of the sample to emit a fluorescence. The fluorescence has a second frequency range and a second time duration, wherein the first time duration is less than the second time duration. A time-resolving detector receives the fluorescence and at least a portion of the white light pulse and separates the fluorescence from the portion of the white light pulse.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses.

In accordance with the teachings of the present disclosure, a method and apparatus is provided employing a single laser source to simultaneously excite a plurality of dye molecules and collect the entire spectrum ranging from visible to near infrared emitted therefrom. Unlike prior art systems, the usefulness of the present teachings is not dependent upon the use of band pass filters and/or dichroic mirrors and, thus, the present teachings provide a significantly simplified optical configuration.

Figure 1:
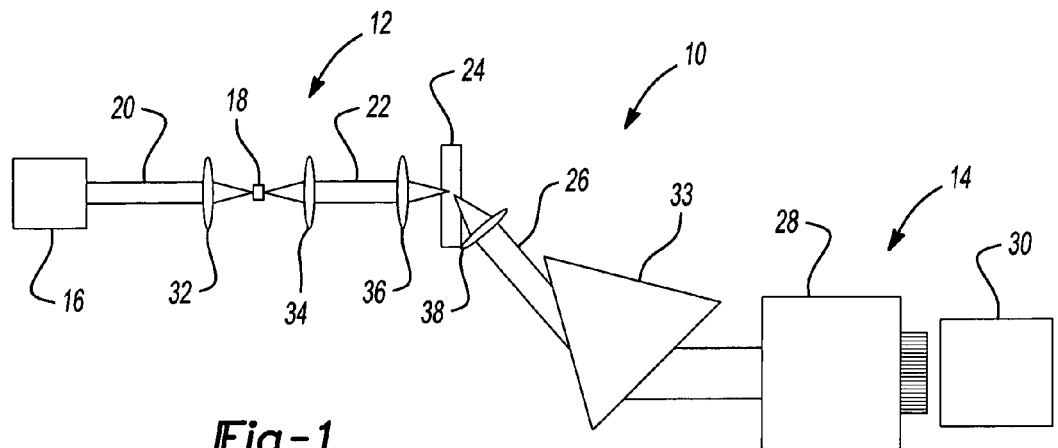
FIG. 1 is a schematic view illustrating a whole spectrum fluorescence detection system according to the principles of the present teachings.

In some embodiments, with particular reference to FIG. 1, a whole spectrum fluorescence detection system 10 can be used for simultaneously detecting multiple fluorophores having various fluorescence frequencies using an ultrafast, supercontinuum, white light pulse 22 source system. Whole spectrum fluorescence detection system 10 can comprise a white light generation system 12 and a detection system 14.

White light generation system 12 can comprise a laser source 16 and a nonlinear material member 18. Laser source 16 can output a high intensity light pulse 20 directed at nonlinear material member 18. Based on the Kerr effect, such high intensity light pulse 20 can pass through and interact with nonlinear material member 18. That is, the nonlinear refractive index of nonlinear material member 18 can modify the optical phase of high intensity light pulse 20, thereby resulting in an ultrafast white light pulse 22. In some embodiments, nonlinear material member 18 can be a sapphire or a photonic crystal fiber. This process can also be described as self-phase modulation. Ultrafast white light pulse 22 can be directed at a sample 24 to be tested.

Although ultrafast white light pulse 22 is very broad in the frequency domain, it is an ultrashort pulse in the time domain. In other words, ultrafast white light pulse 22 can contain a wide spectrum of light frequencies; however, its duration in time is limited and is thus not continuous unlike conventional systems. This limited time duration characteristic of ultrafast white light pulse 22 can be used to separate scattered portions of white light pulse 22 from the resultant fluorescence detected from a sample, which is especially useful when the frequency of the resultant fluorescence overlaps the frequencies of white light pulse 22. By way of non-limiting example, it has been shown that ultrafast white light pulse 22 can have a frequency ranging from visible to near infrared and a pulse duration in the range of about subpicoseconds to a few picoseconds. It has also been found that by employing laser sources 16 having center wavelength shifted to a wavelength shorter than 800 nm, it is possible to extend the spectrum of light frequencies of ultrafast white light pulse 22 in to the ultraviolet region. As a result of the above, the time-dependent phase of high intensity light pulse 20 broadens the resultant spectrum of ultrafast white light pulse 22.

Still referring to FIG. 1, once ultrafast white light pulse 22 is directed at sample 24, excitation of fluorophores contained in sample 24 cause such fluorophores to emit a fluorescence. However, a portion of ultrafast white light pulse 22 may also scatter as a result of various optical effects. Therefore, a combined signal 26 is created having the fluorescence emitted by the fluorophores of sample 24 and the portion of white light pulse 22 that scattered. It should be appreciated that due to the wide spectrum of frequencies contained within ultrafast white light pulse 22, a plurality of fluorophores, each emitting fluorescence in response to excitation at a particular frequency, can simultaneously be excited by virtue of the present teachings. However, it should also be appreciated that many times the plurality of fluorescence generated by the plurality of fluorophores may overlap the frequencies of white light pulse 22. Therefore, it is desirable to separate the plurality of fluorescence from the scattered white light pulse 22 contained in combined signal 26. This separation can be achieved within the time domain.

Figure 3:
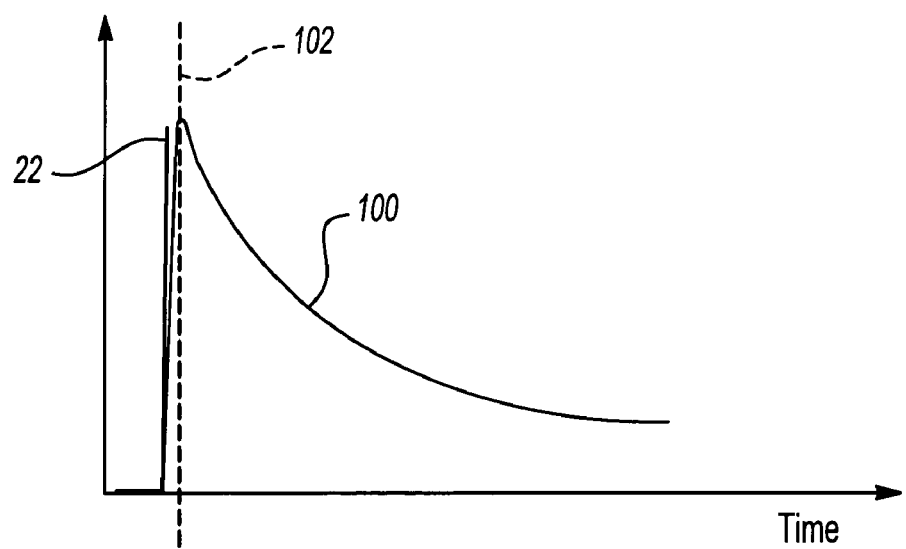
FIG. 3 is a schematic drawing of a white light pulse and excited fluorescence in time domain.
Figure 4:
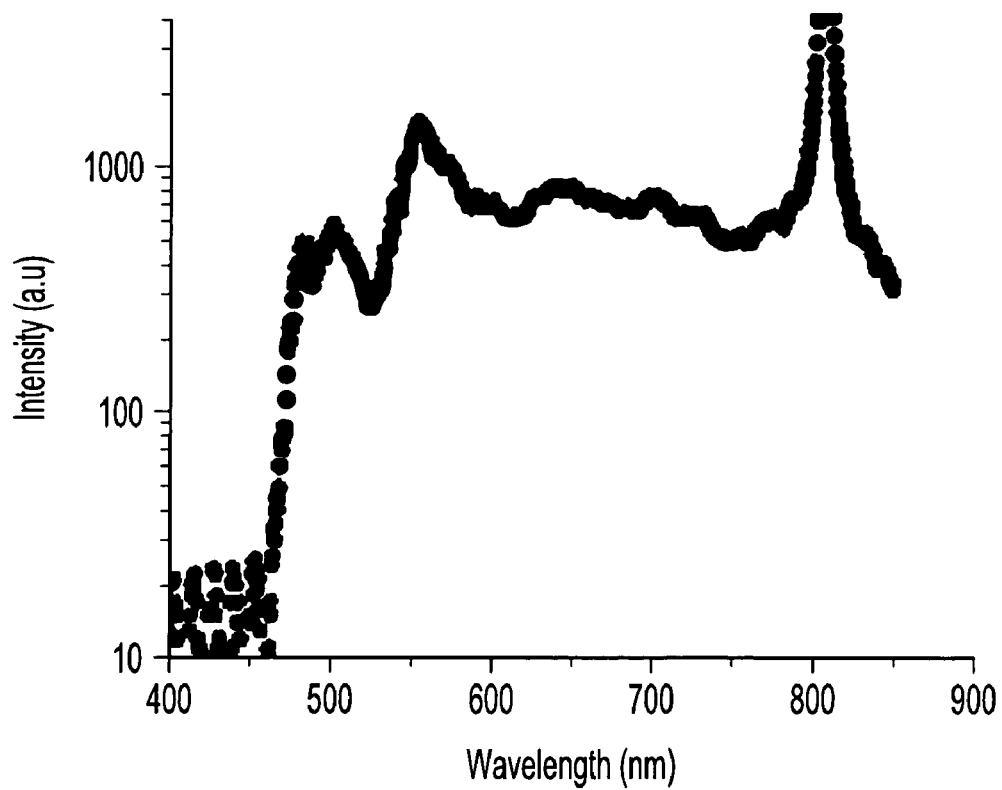
FIG. 4 is a graph illustrating a spectrum distribution of the white light generated using a nonlinear photonic crystal fiber.

As discussed herein and illustrated in FIG. 3, ultrafast white light pulse 22 can have a pulse duration on the order of picoseconds, while the fluorescence, generally indicated at 100, can have a lifetime on the order of nanoseconds. Thus, by using a time-resolving detector 28, such as a streak camera, the scattered portions of white light pulse 22 of combined signal 26 can be screened out while permitting the fluorescence to pass through. The fluorescence can then be detected using a detector 30, such as a CCD, a photomultiplier tube, or the like.

In some embodiments, a plurality of lenses can be used to focus and/or collimate the light pulses as necessary. For example, in some embodiments, a first lens 32 can be used to focus high intensity light pulse 20 onto nonlinear material member 18. A second lens 34 can be used to gather and collimate white light pulse 22 existing nonlinear material member 18. A third lens 36 can be used to focus white light pulse 22 onto sample 24. Finally, a fourth lens 38 can be used to gather and collimate combined signal 26 from sample 24.

In some embodiments, since the fluorescence and white light pulse 22 are different in the time domain, the fluorescence from multiple fluorophores can be wavelength resolved using a prism or grating 33. Therefore, the whole fluorescence spectra can enter the time-resolving detector 28 simultaneously without the need to use any filters or dichroic mirrors. This new fluorescence detection technique of the present teachings not only allows one to excite a large variety of fluorophores in a wide wavelength range, but also significantly simplifies the system configuration by using a single laser source and eliminating the requirements of using many sets of filters and dichroic mirrors as used in conventional fluorescence detection systems.

Figure 2:
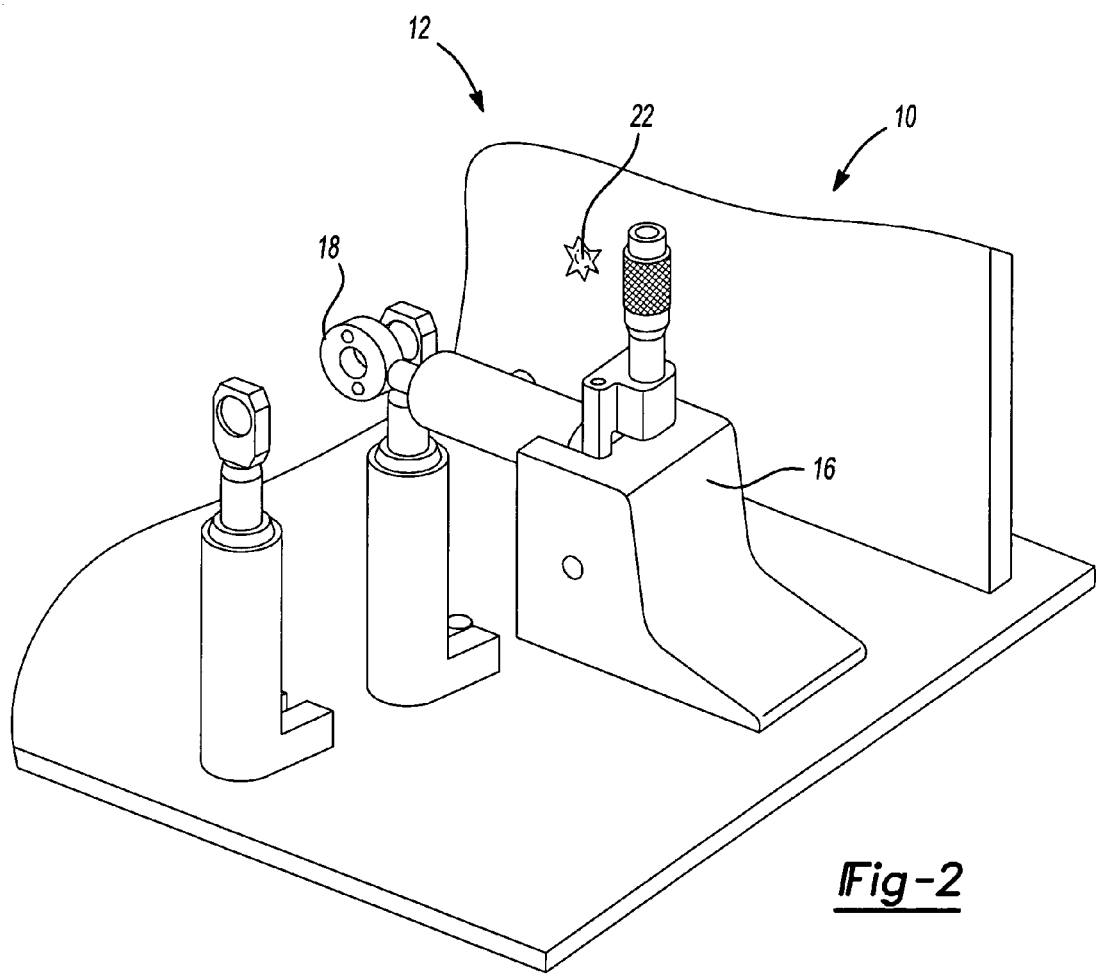
FIG. 2 is a perspective view illustrating the white light generation used in the whole spectrum fluorescence detection system of FIG. 1 with portions removed for clarity.

In some embodiments, as illustrated in FIG. 2, laser source 16 can comprises a modified 250-kHz regeneratively amplified Ti:sapphire laser. High intensity light pulse 20 can define a pulse duration of about 100 femtoseconds and wavelength of 793 nm. High intensity light pulse 20 can then be focused onto a sapphire (nonlinear material member 18) to generate ultrafast white light pulse 22. The resultant spectrum of ultrafast white light pulse 22 can include the entire spectrum of visible light and at least a portion of infrared light, and, in some embodiments, at least a portion of ultraviolet light. In some embodiments, ultrafast white light pulse 22 can be generated using a Ti:sapphire oscillator without regenerative amplifier by focusing high intensity light pulse 20 from laser source 16 on to a nonlinear photonic crystal fiber (PCF) (nonlinear material member 18).

Figure 7:
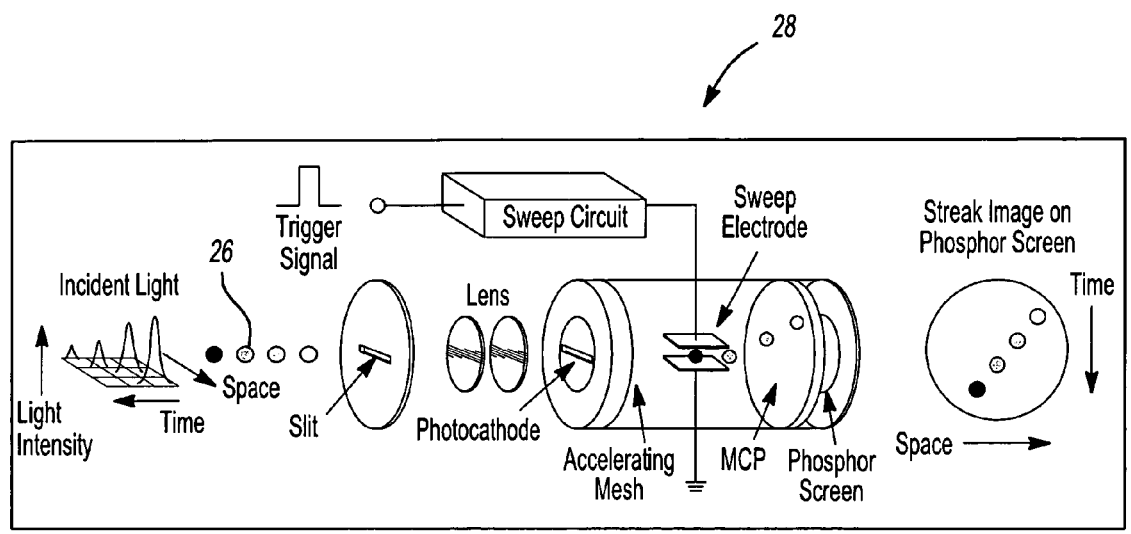
FIG. 7 is a schematic view illustrating a streak camera that can be used in some embodiments of the present teachings.

In some embodiments, time-resolving detector 28 can be a streak camera, available from HAMAMATSU, to separate the fluorescence signals from white light pulse 22 in the time domain. Briefly, as illustrated in FIG. 7, a streak camera is a device which can detect time-resolved fluorescence spectrum. The incident light, which in the present teachings contains both the fluorescence and scattered portions of white light pulse 22, is focused into a slit and arrived at a photocathode of a streak camera. The number of electrons generated is proportional to the timing and the intensity of the incident light. The electrons then pass between a pair of sweep electrodes, where varying high voltage is applied at a timing synchronized to the incident light. Thus, the deflection angle of the electrons by the high sweep voltage depends on the timing when the electrons got into this zone. A micro-channel plate (MCP) is placed behind the sweep electrodes to multiply the electrons by several thousands of times. Then the amplified electrons impact against a phosphor screen and convert into light signals, which can be detected with a CCD camera or a photomultiplier tube.

Figure 5A:
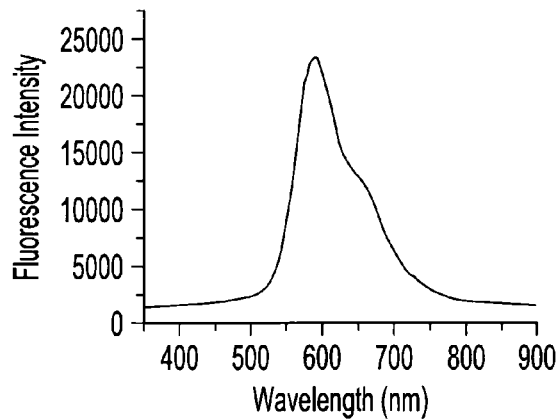
FIG. 5(a) is a graph illustrating a spectrum distribution of Kiton Red.
Figure 5B:
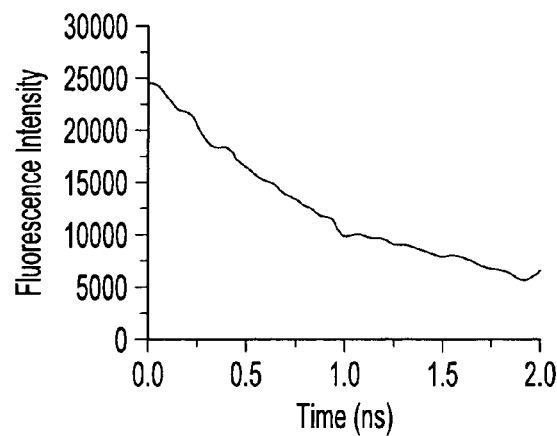
FIG. 5(b) is a graph illustrating a flourescence decay curve for Kiton Red.

In the present teachings, the delay line 102 (see FIG. 3) is varied such that white light pulse 22, which is at the front of each incident pulse (see FIG. 3), is deflected by the sweep electrodes to an angle outside the MCP detection region. Consequently, the scattered portions of white light pulse 22 are separated from the fluorescence, generally referred to as an isolated fluorescence signal 40. Thus, the light signal coming out of the phosphor screen is purely proportional to the fluorescence signals. As an example, FIG. 5(a) illustrates the fluorescence spectrum of Kiton Red detected with a CCD attached to the output port of the streak camera. In addition, the fluorescence decay curve is also obtained simultaneously using the streak camera, as illustrated in FIG. 5(b).

It should be understood that the wide spectrum range of ultrafast white light pulse 22 can enable a large number of different kinds of fluorophores having absorption falling within this spectrum range can be excited. It has been found that such dye molecules as coumarin 343, fluorescein, Rhodamin 6G, Kiton Red, and LDS 698 having fluorescence emission ranging from about 450 to about 690 nm can be excited with the single ultrafast white light source of white light generation system 12.

The present teachings provide a unique approach for fluorescence excitation and detection in contrast to conventional fluorescence measurements. While the present teachings can provide a new range of possible applications, they can also be integrated into many other existing fluorescence detection instruments, including spectrofluorometers and microplate readers, fluorescence microscopes, endoscopes, and flow cytometers, etc. The applicability of the present teachings in these areas will become apparent from the discussion set forth herein.

Application in Flow Cytometry

With nearly 40-year track record of being the most accurate and well-defined technology for measuring properties of single cells, flow cytometry might appear to be commonplace and mature, but it has not reached the pinnacle of its capability. In order to simultaneously detect a large variety of cells stained with different fluorescent markers, researchers often attempt to increase the number of excitation sources and detection channels. For example, BD Biosciences, a leading biotechnology company, recently produced the most sophisticated commercially available system, the BD FACSAria, which has three lasers with wavelengths at 488 nm, 633 nm, and 407 nm as the excitation sources, and has a complicated signal collection system composed of 20-30 sets of filters and dichroic mirrors and 14 photomultiplier tube detectors. In spite of the complexity, this expensive flow cytometer is not capable of exciting all fluorescent markers in the visible and near infrared region due to the limited available excitation wavelengths. In practice, it is almost impossible to further increase the number of lasers for excitation due to the limited unit size and complicated optical configurations necessary.

In contrast, employing the principles of the present teachings, a single laser source can provide the necessary excitation of different fluorescent biomarkers in the whole visible and near infrared region. In addition, employing the teachings of the present invention, no filters and/or dichroic mirrors are required. This unique way of fluorescence detection has significantly simplified the optical configuration and enhanced the instrument performance for multi-color, multi-parameter flow cytometry.

Figure 6A:
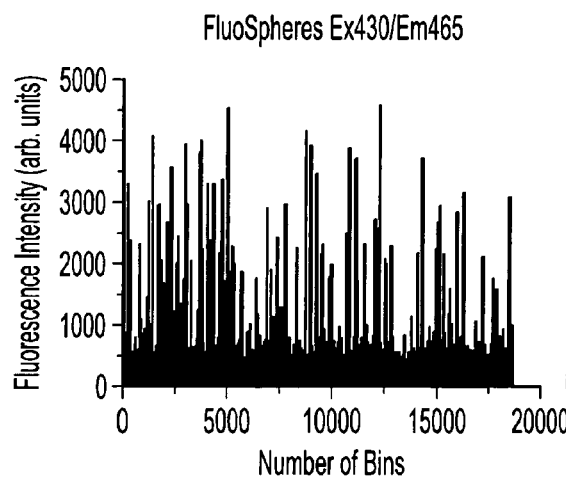
FIG. 6(a) is a graph illustrating measurements of Fluo-Spheres Ex430/Em465 following excitation from the white light generation system of the present teachings.
Figure 6B:
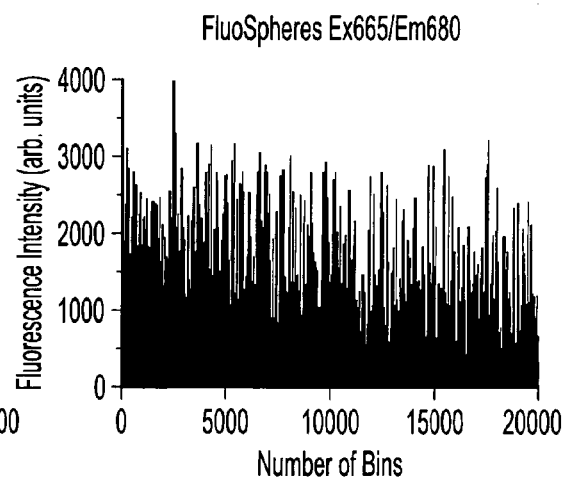
FIG. 6(b) is a graph illustrating measurements of Fluo-Spheres Ex665/Em680 following excitation from the white light generation system of the present teachings.

It has been demonstrated that fluorescent beads with different absorption and emission wavelength can be measured in whole spectrum fluorescence detection system 10 without changing either the excitation source or filters. That is, a flow system was used during such demonstrating consisting of a square fused silica capillary (available from Polymicro Technologies Inc.) and a syringe pump. The square fused silica capillary, having a 100 micrometers inner diameter and a 300 micrometers outer diameter, was prepared by burning away about a 2 cm patch of the polyimide coating in the center of a 30 cm long piece. The square capillary was held perpendicular to ultrafast white light pulse 22 with its surface adjusted flat to white light generation system 12. The capillary was connected to a syringe pump (available from Fisher Scientific) with plastic tubing. Fluorescent micro-sphere samples were loaded into a syringe and pushed by the syringe pump through the capillary at a constant flow rate of about 5 µL/minute. Fluorescence was collected at a right angle to the capillary and white light generation system 12, and detected with a streak camera as described herein. FIG. 6(a) illustrates the resultant fluorescence signals from 10-µm fluorescent beads having an absorption maximum of 430 nm and an emission maximum of 465 nm. Similarly, FIG. 6(b) illustrates the resultant flourescence signals from fluorescent beads having an absorption maximum of 665 nm and an emission maximum of 680 nm. Each peak of FIGS. 6(a)-(b) represents a fluorescence burst from an individual sphere passing through the excitation volume. As can be seen from FIGS. 6(a)-(b), whole spectrum fluorescence detection system 10, or at least white light generation system 12, can provide whole spectrum excitation and/or detection, and thereby significantly enhance the applications of flow cytometers for true multi-color and multi-parameter analysis. Whole spectrum fluorescence detection system 10, or at least white light generation system 12, can further enable exploration of new biomarkers in a wavelength region that is otherwise not possible to be accessed with conventional flow cytometers.

Applications in Fluorescence Screening

Fluorescence screening has been widely used to find potential drug leads, to monitor food safety, and to monitor human health conditions. For instance, the drug-binding efficiency of a candidate compound can be estimated with fluorescence measurements based on the effect that the binding of a drug to an antigen can affect the emission spectrum of a fluorophore bound to the antigen, or can induce or quench fluorescence from that fluorophore. Because there is normally an extensive library of compounds to be tested, whole spectrum fluorescence detection system 10 having white light generation system 12 and detection system 14 enable the fluorescence screening of different compounds simultaneously without a need to modify instrument settings and/or conduct multiple tests. This will dramatically reduce the screening time and accelerate the drug development process. Accordingly, it is believed that the integration of the present teachings to currently commercially available fluorescence screening instruments can realize an extremely high-throughput screening, which is demanded for many applications.

Application in Fluorescence Microscopy

Fluorescence microscopes are a powerful tool being widely used in cell biology. The advent of confocal microscopes has enabled one to locate fluorescent biomarkers in three dimensions within a cell. Further studies of distributions or behaviors of multiple probes in the same cells have been made possible by the development of confocal microscopes that are capable of efficiently collecting multiple colors of fluorescence and developing new dyes that have extended the useful spectrum of fluorescence microscopy. Such a multi-color confocal microscope generally requires using multiple lasers for excitation and complicated detection systems. However, the present teachings enable the use of a single excitation source to provide a true whole spectrum fluorescence microscopy with a simple optical configuration by using white light generation system 12 for excitation and time-resolving detector 28, such as a streak camera, to separate fluorescence signals from white light pulse 22.

What is claimed is:

1. A fluorescence detection system for testing a sample, said sample having a plurality of fluorophores, said fluorescence detection system comprising:
    a single-source white light generation system outputting a supercontinuum white light pulse comprising an entire spectrum of white light, said supercontinuum white light pulse exciting the plurality of fluorophores of the sample to emit fluorescence; and
    a time-resolving detector receiving said fluorescence and at least a portion of said supercontinuum white light pulse, said time-resolving detector separating said fluorescence from said portion of said supercontinuum white light pulse.

2. The fluorescence detection system according to claim 1 wherein said white light generation system comprises:
    a laser source outputting a laser pulse; and
    a member having a non-linear refractive index, said member receiving said laser pulse therethrough and outputting said supercontinuum white light pulse.

3. The fluorescence detection system according to claim 2 wherein said laser source is a Ti:sapphire laser.

4. The fluorescence detection system according to claim 2 wherein said member is a sapphire.

5. The fluorescence detection system according to claim 2 wherein said member is a photonic crystal fiber.

6. The fluorescence detection system according to claim 1 wherein a frequency of said supercontinuum white light pulse and a frequency of said fluorescence at least partially overlap.

7. The fluorescence detection system according to claim 1 wherein said time-resolving detector is a streak detector.

8. The fluorescence detection system according to claim 1 wherein said time-resolving detector comprises a device operable to define a delay time duration that is equal to or greater than a duration of said supercontinuum white light pulse, said time-resolving detector isolating said fluorescence from said portion of said supercontinuum white light pulse based on said delay time duration to output an isolated fluorescence signal.

9. The fluorescence detection system according to claim 8, further comprising:
    a prism member receiving said fluorescence and distributing said fluorescence based upon a frequency thereof.

10. A fluorescence detection system for testing a sample, said sample having a plurality of fluorophores, said fluorescence detection system comprising:
    a single laser source outputting a laser pulse having a first time duration;
    a member having a non-linear refractive index, said member receiving said laser pulse therethrough and outputting a supercontinuum white light pulse comprising an entire spectrum of white light, said supercontinuum white light pulse having a first frequency range and a second time duration, said supercontinuum white light pulse exciting the plurality of fluorophores of the sample to emit fluorescence, said fluorescence having a second frequency range and a third time duration, said second time duration being less than said third time duration; and
    a time-resolving detector receiving said fluorescence and at least a portion of said supercontinuum white light pulse, said time-resolving detector separating said fluorescence from said portion of said supercontinuum white light pulse.

11. The fluorescence detection system according to claim 10 wherein said first time duration is equal to said second time duration.

12. The fluorescence detection system according to claim 10 wherein said laser source is a Ti:sapphire laser.

13. The fluorescence detection system according to claim 10 wherein said member is a sapphire.

14. The fluorescence detection system according to claim 10 wherein said member is a photonic crystal fiber.

15. The fluorescence detection system according to claim 10 wherein said first frequency range and said second frequency range at least partially overlap.

16. The fluorescence detection system according to claim 10 wherein said time-resolving detector is a streak detector.

17. The fluorescence detection system according to claim 10 wherein said time-resolving detector comprises a device operable to define a delay time duration that is equal to or greater than said second time duration, said time-resolving detector isolating said fluorescence from said portion of said supercontinuum white light pulse based on said delay time duration to output an isolated fluorescence signal.

18. The fluorescence detection system according to claim 17, further comprising:
    a prism member receiving said fluorescence and distributing said fluorescence based upon a frequency thereof.

19. A fluorescence detection system for testing a sample, said sample having a first fluorophore and a second fluorophore, said fluorescence detection system comprising:

a single-source white light generation system outputting a supercontinuum white light pulse comprising an entire spectrum of white light, said supercontinuum white light pulse having a first frequency range and a first time duration, said supercontinuum white light pulse exciting the first fluorophore and the second fluorophore to emit a first fluorescence and a second fluorescence respectively, said first fluorescence having a second frequency range that is different than a third frequency range of said second fluorescence, said first fluorescence having a second time duration and said second fluorescence having a third time duration, said first time duration being less than said second time duration and said third time duration; and a time-resolving detector receiving said first fluorescence, said second fluorescence, and at least a portion of said supercontinuum white light pulse, said time-resolving detector separating said first fluorescence and said second fluorescence from said portion of said supercontinuum white light pulse.

20. The fluorescence detection system according to claim 19 wherein said white light generation system comprises:
a laser source outputting a laser pulse; and
a member having a non-linear refractive index, said member receiving said laser pulse therethrough and outputting said suoercontinuum white light pulse.

21. The fluorescence detection system according to claim 20 wherein said laser source is a Ti:sapphire laser.

22. The fluorescence detection system according to claim 20 wherein said member is a sapphire.

23. The fluorescence detection system according to claim 20 wherein said member is a photonic crystal fiber.

24. The fluorescence detection system according to claim 19 wherein said first frequency range at least partially overlaps with at least one of said second frequency range and said third frequency range.

25. The fluorescence detection system according to claim 19 wherein said time-resolving detector is a streak detector.

26. The fluorescence detection system according to claim 19 wherein said time-resolving detector comprises a device operable to define a delay time duration that is equal to or greater than said first time duration, said time-resolving detector isolating said first fluorescence and said second fluorescence from said portion of said supercontinuum white light pulse based on said delay time duration to output an isolated fluorescence signal.

* * * * *